United States Patent [19]

Ketel, II

[11] 4,412,444
[45] Nov. 1, 1983

[54] METHOD FOR DETECTION OF HYDROCARBONACEOUS FUEL IN A FUEL INJECTION ENGINE

[75] Inventor: William E. Ketel, II, Royal Oak, Mich.

[73] Assignee: Sun Electric Corporation, Crystal Lake, Ill.

[21] Appl. No.: 335,348

[22] Filed: Dec. 29, 1981

[51] Int. Cl.³ .............................................. G01N 27/12
[52] U.S. Cl. ......................................... 73/23; 123/438
[58] Field of Search .............. 73/23; 340/634; 422/98; 123/438, 440, 489

[56] References Cited

U.S. PATENT DOCUMENTS

| 3,625,756 | 12/1971 | Taguchi | 427/87 |
| 3,631,436 | 12/1971 | Taguchi | 340/634 |
| 3,644,795 | 2/1972 | Taguchi | 338/34 |
| 3,676,820 | 7/1972 | Taguchi | 338/34 |
| 3,695,845 | 10/1972 | Watz | 436/148 |
| 3,732,519 | 5/1973 | Taguchi | 338/34 |
| 3,835,529 | 9/1974 | Taguchi | 29/570 |
| 3,900,815 | 8/1975 | Taguchi | 338/34 |
| 4,050,425 | 9/1977 | Holleboom | 123/438 |

Primary Examiner—Stephen A. Kreitman
Attorney, Agent, or Firm—Allegretti, Newitt, Witcoff & McAndrews, Ltd.

[57] ABSTRACT

A method and apparatus for detecting the presence and quantity of fuel in a fuel/air mixture to the cylinders of a fuel injection engine is disclosed. A portion of the fuel/air mixture injected to the engine is diverted through a solid state sensor which, when included in a detection circuit, provides a resistance which is proportional to the amount of fuel in the mixture. The sensor reacts to the presence of the fuel vapors by providing a change in the voltage across the sensor.

10 Claims, 3 Drawing Figures

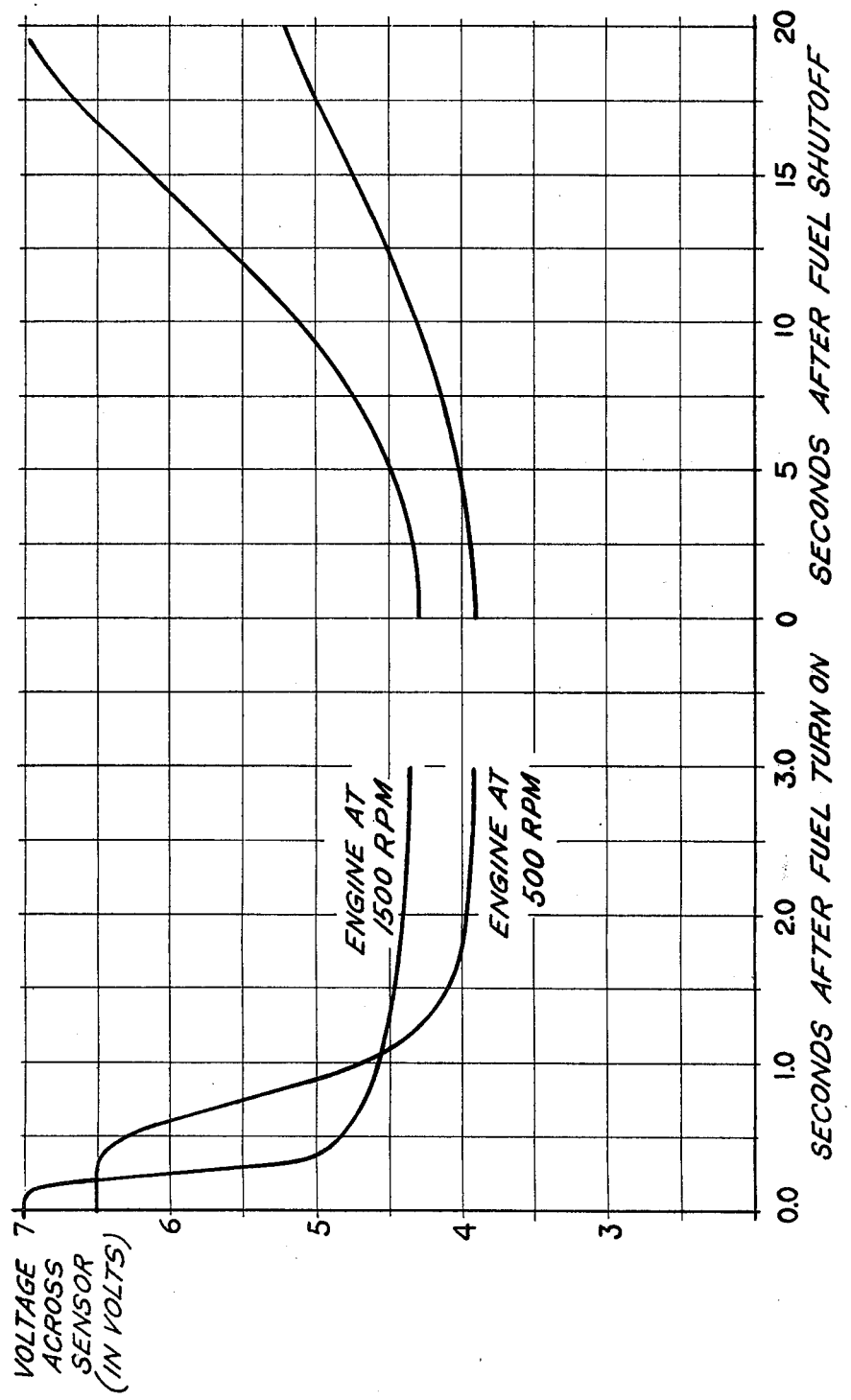

METHOD FOR DETECTION OF HYDROCARBONACEOUS FUEL IN A FUEL INJECTION ENGINE

BACKGROUND OF THE INVENTION

This invention relates to a method for detecting the presence of hydrocarbonaceous fuel and, more particularly, to a method for detecting the presence of hydrocarbonaceous fuel in the fuel inlet line to the cylinders of a fuel injection engine.

In fuel injection engines an air/fuel mixture is directed from an inlet line into the engine cylinders for combustion. It is desirable to be able to detect the presence and amount of fuel in the inlet line to the engine cylinders as part of the engine throttle control system so that efficient operation of the engine can be maintained. It is also desirable to be able to detect the amount of fuel being provided for combustion while the engine is on a production line engine test stand, so that efficient operation of the engine can be tested prior to the engine being installed in a vehicle.

A known prior art fuel detection system is the "hot wire" method of gas detection which examines the cooling effect of a fuel mist. This method involves heating a wire by running a constant current through it. A sample stream of fuel mist is directed across the wire. The voltage across the wie is measured to determine how much heat is removed from the wire by the sample stream. The greater the amount of heat removed by the sample stream, the greater the concentration of fuel mist in the stream.

Optical methods for detecting fuel mist have also been used in the prior art. These methods utilize an opacity meter for use with a sample stream containing exhaust from an operating engine. As the concentration of fuel particles in the exhaust increases, the transmission of light through the stream is reduced and light scattering is increased.

A problem associated with the prior art methods for fuel detection is that the systems are generally used solely as safety equipment and, consequently, do not have fast response or recovery times. Also the detection system, usually in the form of an alarm, must be reset after the presence of fuel or vapor is detected and the alarm is sounded. These methods have not been useful for testing continuously operating fuel injection engines or other equipment which utilizes fuel.

SUMMARY OF THE INVENTION

It has now been discovered that the presence of fuel in a fuel injection engine can be detected through the use of a gas or fuel sensing element, or sensor, rather than by the monitoring of a physical property of the fuel such as electroconducting or cooling effect. Thus, a vapor laden air stream from the fuel line to the engine cylinders is passed by a diverter at high velocity. A small portion of the air stream is directed by the diverter to a sensor housing at a lower velocity. The sensor is part of an electrical circuit which includes a device for monitoring voltage changes in the circuit. By quantitatively measuring voltage changes, the presence and amount of hydrocarbonaceous fuel vapors in the air stream can be continuously detected.

Accordingly, it is an object of the present invention to provide a method and apparatus for detecting the presence of fuel in a fuel injection line to the cylinders of an engine to determine whether the injection system is delivering fuel to each cylinder of the fuel injection engine.

Another object of the present invention to provide a method and apparatus for detecting the presence of fuel in a fuel injection engine by chemical means rather than by detecting a physical property of the fuel.

A further object of the present invention is to provide a method and apparatus for detecting the presence of fuel in a fuel injection engine which may be incorporated in production line engine test stands.

Still another object of the present invention is to provide a method and apparatus for detecting fuel in a fuel injection engine having a faster response time for detection of the fuel than known prior art systems.

Yet another object of the present invention is to provide a method and apparatus for detecting the presence of fuel in a fuel injection engine which is characterized by fast recovery of the sensor in the sensing system through the prevention of overloading the sensing system with excess hydrocarbons.

These and other objects, advantages and features of the invention will be set forth in the detailed description which follows.

BRIEF DESCRIPTION OF THE DRAWING

In the detailed description which follows, reference is made to the drawing comprised of the following figures:

FIG. 3 is a graph of typical voltage changes detected by the sensing system when a sample stream from the fuel injection engine flows through the sensing system.

DETAILED DESCRIPTION OF THE PREFERRED EMBODIMENT

Figure 1:
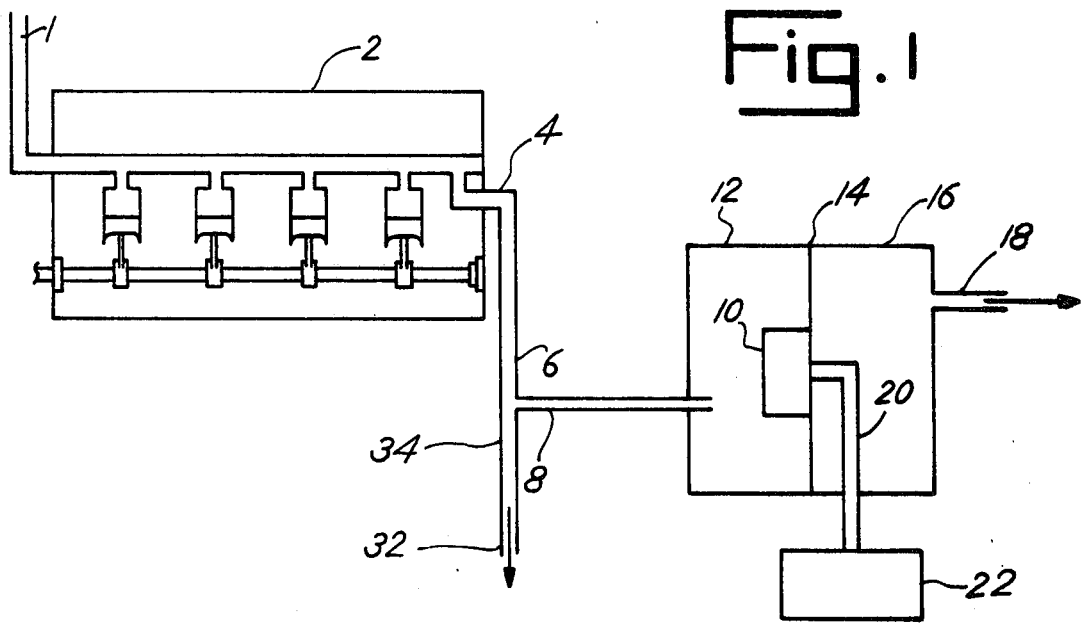
FIG. 1 is a schematic diagram of the fuel detection system of the present invention which detects the presence of fuel in a fuel injection engine.

FIG. 1 illustrates a fuel detection system for detecting the presence and amount of fuel in the cylinders of a fuel injection engine. A fuel/air mixture from the fuel inlet line 1 to the cylinders 3 of a fuel injection engine 2 passes into a sample tube 4. Sample tube 4 extends from the fuel inlet line when the fuel injection engine is in operation and fuel is being combusted.

Alternatively, when there is no combustion taking place in the engine, sample tube 4 can extend from the gloplug ports of engine 2, if no plugs are utilized. Sample tube 4 can also extend from the exhaust manifold of engine 2 when no ignition in the cylinders is occurring. In each event, a sample of the fuel mixture to the cylinders is to be provided.

The fuel/air mixture forms a fuel vapor laden stream which moves through tube 4 to a diverter 6 at a high velocity in excess of 100 feet/second. Most of the stream flows past the diverter 6, which is a reduced tee fitting, and out through vent tube 32 to a standard fume collection system, such as a negative pressure vent system containing a duct leading to an exhaust fan with vapor filters positioned in the vent line. In this manner, the fuel vapor can be recaptured and recycled when the engine 2 is on a production test stand.

A small portion of the stream is diverted by diverter 6 into a short sample tube 8. This small portion of the stream flows through sample tube 8 at a low velocity of approximately 5 feet/second. The low velocity is attained because diverter 6 directs a sufficiently small volume of air and vapor into sample tube 8 to allow a reduction in velocity.

The vapor laden stream is then slowed to a still lower velocity in the last inch of the sample tube 8, before entry into a sensor chamber 12 which houses a sensor 10. The air stream attains the still lower velocity due to the stream passing from sample tube 8 into the sensor chamber 12, which has a greater cross-sectional dimension than does sample tube 8. This final deceleration is necessary, since the output and sensitivity of sensor 10 decreases as the velocity of the air stream increases. Therefore, it is desirable to minimize variances in output by having the air stream flow into sensor 10 with a minimum velocity. This avoids the use of circuitry or logic to compensate for variances in output.

A portion of the vapor laden stream then flows into sensor 10, passes through the sensor 10 and into a rear portion 16 of the sensor chamber 12, where it exits via vent tube 18 to a fume collection system as previously described herein.

The sensor 10 is supported or mounted in the sensor chamber 12 by a mounting plate 14. The sensor 10 is connected by wiring 20 to external electronics, which are described in greater detail hereinafter, and to a monitor 22, which may be an amplifier, a computer, such as programmable controller or any other type of voltage monitoring device.

The sensor 10 has fast reponse and recovery times since no particulate hydrocarbons contained in the fuel vapor are permitted to reach the sensor. This is quite important as particulate matter entering sensor 10 can prevent the sensor 10 from functioning efficiently. The particulate hydrocarbons contained in the fuel vapor do not reach the sensor 10 since the fuel-containing stream, passing through sample tube 8, is at a sufficiently low velocity such that the particulate hydrocarbons, which are heavier than the vapor, cannot be carried along in the air stream. In addition, the low velocity air stream prevents any significant alteration of the temperature equilibrium of the sensor 10.

Thus, hydrocarbon particules or droplets are first eliminated at the diverter 6, where the sample destined for the sensor 10 undergoes a 90° change in the direction of its flow due to its passing through the diverter 6, which has a þtee" configuration, and, therefore, simultaneously has its velocity reduced.

The diverter 6 is mounted so that the sample air stream destined for the sensor 10 leaves vertically and travels upwards about one foot before entering the sensor 10, which is mounted horizontally. In a preferred embodiment of the invention, the sample tube 4 through the diverter 6 has approximately ten times the cross sectional diameter of the sample tube 8 from the diverter 6 to the sensor 10, and there is very little back pressure on the bypass line 34 from the diverter 6 to the vent 32.

The particles or droplets which enter sample tube 8 fall, due to the low velocity of the air stream, and are picked up by the high velocity air stream and are exhausted through vent 32 to a suitable exhaust collection system. Any remaining particles or droplets are removed in the sensor housing 12, where the sample air stream undergoes its final deceleration, due to the stream passing into the housing 12, which has a greater cross-sectional diameter than does sample tube 8. This causes any particles or droplets to bypass the sensor 10.

Figure 2:
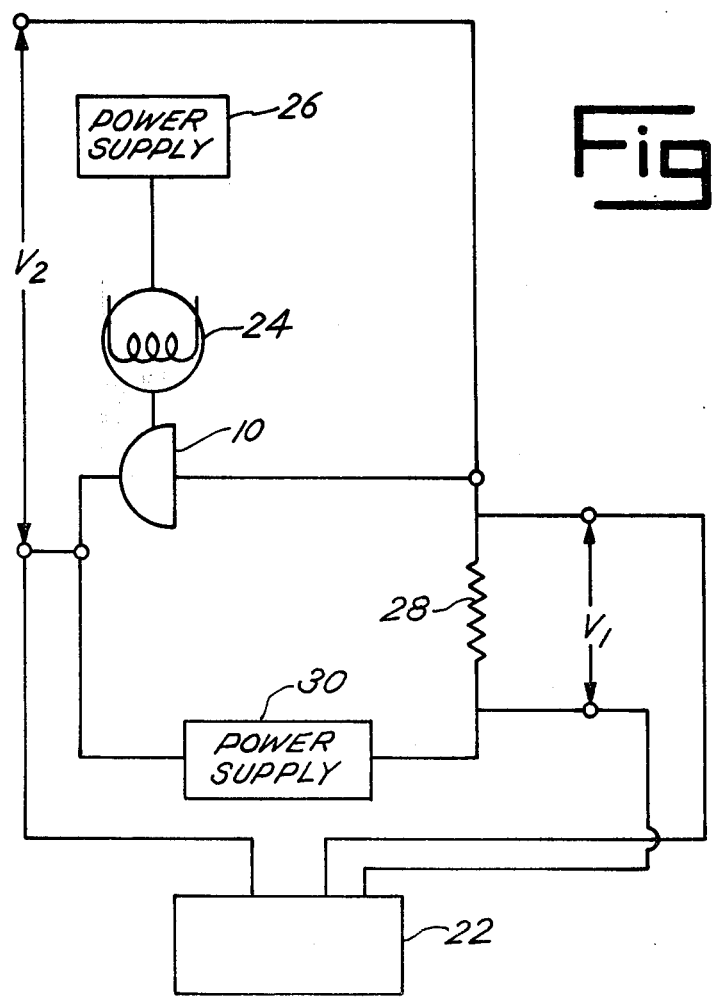
FIG. 2 is an electrical schematic circuit diagram of the sensing system of the present invention which is utilized for detecting the presence of fuel in a fuel injection engine.

With reference to FIG. 2, the sensing system for detecting the presence of fuel vapors is illustrated. The temperature of the sensor 10 is maintained by a heater 24, which is connected to a power supply 26. When voltage is applied to the sensor 10 by power supply 30, a voltage $V_1$ is developed across load resistor 28, and a voltage $V_2$ is also developed across the sensor 10. When fuel vapors are present in the air stream entering the sensor 10, this causes the resistance of sensor 10 to decrease and $V_1$ to increase. At the same time, $V_2$ decreases.

The voltage monitor or amplifier 22 is connected to the circuit to monitor voltages $V_1$ and $V_2$ for control purposes. A change in either voltage, $V_1$ or $V_2$, typically, of at least two volts, as monitored by amplifier 22, determines the presence of the fuel vapors flowing into the cylinders of engine 2.

FIG. 3 illustrates a graphical representation of the response of the sensor 10 when used in the method of the present invention. Tests were run using a typical V-8 diesel engine at two different speeds, 500 rpm and 1500 rpm.

In FIG. 3, the ordinate depicts the voltage, in volts, across sensor 10 as monitored by amplifier 22. The left side of the abscissa depicts time, in seconds, after fuel begins to flow into the cylinders of engine 2. The right side of the abscissa depicts time, in seconds, after the fuel flow to the cylinders is shut off. FIG. 3 shows that the voltage change across sensor 10 is approximately 2.5-3.0 volts over a period of 3 seconds after fuel flow into the cylinders of engine 2 begins. As can be seen with reference to FIG. 3, the response was good at both speeds.

It must be noted that the amount of voltage change across sensor 10 is relatively independent of the velocity of the fuel vapor-laden air stream as it flows into sensor 10, and the type of hydrocarbonaceous fuel being used.

It is presumed that one skilled in the art can generate such graphs for fuels and flow rates other than those used to generate the data shown in FIG. 3.

A sensor that has been found satisfactory for use in the present invention is the TGS-812 Gas Sensor of Figaro Engineering Inc. This is a fuel vapor sensitive semiconductor of the type disclosed in Taguchi, U.S. Pat. No. 3,900,815. In a gas sensing device of the type described in Taguchi, a powdered metal oxide semiconductor material is mixed with a material, such as stearic acid, which evaporates, sublimates or burns away when heated and produces a number of holes therein. The mixture is applied to a ceramic supporting material and is then heated at an elevated temperature. The resulting metal oxide semiconductor material is disposed between two electrodes to form the gas sensing element. The gas sensing element is used as an alarm device to detect gas leaks for safety purposes. The sensor has a signal output of several volts without amplification.

There has been provided by the present invention a method and apparatus for detecting the presence of fuel vapors in the cylinders of a fuel injection engine chemically rather than detecting a physical property of the fuel. The novel method and apparatus of this invention can be utilized with an engine production test stand and facilitates fast response and recovery times in the sensing system.

It should be understood that the foregoing disclosure emphasizes certain specific embodiments of the invention and that all modifications or alternatives equivalent thereto are within the spirit or scope of the invention as set forth in the appended claims.

I claim as my invention:

1. A method for detecting the presence of hydrocarbonaceous fuel in the fuel injection flow through the fuel line to the cylinders of a fuel injection engine comprising the steps of:
   (a) diverting a portion of the flow through the fuel line into a sample tube;
   (b) reducing the rate of flow of the diverted portion to a rate of 3-6 feet/second;
   (c) passing the reduced flow over a sensor of the type comprising a fuel vapor sensitive semiconductor having a signal output proportional to the quantity of fuel vapor in the flow;
   (d) providing means for monitoring the sensor signal including a programmable controller; and
   (e) monitoring quantitatively the sensor signal change to detect the presence and amount of said hydrocarbonaceous fuel.

2. The method of claim 1 including the additional step of decelerating the reduced flow to a rate of less than 3 feet/second immediately prior to the flow passing over the sensor.

3. The method of claim 2 wherein the additional step of decelerating the reduced flow comprises decelerating the reduced flow at a distance of approximately one inch from the sensor, thereby minimizing the rate of flow into the sensor.

4. The method of claim 1 wherein said step of monitoring comprises electrically connecting the sensor to a resistor, applying a voltage across said sensor and said resistor and quantitatively monitoring the change in voltage across said sensor and said resistor.

5. An apparatus for detecting the presence of hydrocarbonaceous fuel in the fuel injection flow through the fuel line to the cylinders of a fuel injection engine comprising, in combination:
   (a) a first sample tube connected from the fuel line for receipt of a portion of the fuel line flow and defining a stream containing said hydrocarbonaceous fuel in a substantially vapor state and hydrocarbonaceous particulate matter passing therein;
   (b) a second sample tube connected to the first sample tube and having an outlet end and a lesser diameter than the first sample tube;
   (c) means for diverting a sample of the flow in said first sample tube to the second sample tube to reduce the rate of flow of said sample in said second sample tube; and
   (d) means for detecting the presence of the hydrocarbonaceous fuel, said means for detecting connected to said outlet end of said second sample tube and including a chamber for reducing the flow rate from the second sample tube and an exhaust passage from the chamber.

6. The apparatus of claim 5 wherein said means for detecting the presence of the hydrocarbonaceous fuel comprises a sensor in the chamber connected in an electrical circuit, said circuit including at least one resistor connected in series with said sensor, a power supply connected across said sensor and said resistor to provide a voltage and voltage monitoring means for monitoring changes in voltage drop across the sensor.

7. The apparatus of claim 6 wherein said sensor is a gas sensitive semiconductor.

8. The apparatus of claim 7 including heating means for controlling the temperature of said sensor.

9. The apparatus of claim 5 wherein said first sample tube has a cross-sectional diameter of approximately ten times the cross-sectional diameter of said second sample tube.

10. The apparatus of claim 6 wherein said voltage monitoring means is a programmable controller.

* * * * *